US011172856B2

(12) United States Patent
Korkor, II et al.

(10) Patent No.: US 11,172,856 B2
(45) Date of Patent: Nov. 16, 2021

(54) SYSTEMS AND METHODS FOR UROFLOWMETRY

(71) Applicant: Emano Metrics, Inc., Eugene, OR (US)

(72) Inventors: Bishara Charles Korkor, II, Eugene, OR (US); Alan Reid Hay, Anchorage, AK (US); Edouard Alan Hay, Eugene, OR (US)

(73) Assignee: Emano Metrics, Inc., Eugene, OR (US)

( * ) Notice: Subject to any disclaimer, the term of this patent is extended or adjusted under 35 U.S.C. 154(b) by 0 days.

(21) Appl. No.: 16/810,221

(22) Filed: Mar. 5, 2020

(65) Prior Publication Data

US 2021/0275073 A1    Sep. 9, 2021

(51) Int. Cl.
*A61B 5/20* (2006.01)
*G10L 25/66* (2013.01)
*G06T 7/174* (2017.01)
*A61B 5/00* (2006.01)
*G06T 7/00* (2017.01)

(52) U.S. Cl.
CPC ............ *A61B 5/208* (2013.01); *A61B 5/7267* (2013.01); *A61B 5/742* (2013.01); *A61B 5/7475* (2013.01); *G06T 7/0012* (2013.01); *G06T 7/174* (2017.01); *G10L 25/66* (2013.01); *G06T 2207/30004* (2013.01)

(58) Field of Classification Search
CPC .............. G01N 33/483; G01N 33/487; G01N 33/48707; G01N 33/48792; G01N 33/48785; G01N 33/493; A61B 5/7267; A61B 5/6891; A61B 58/20; A61B 5/201; A61B 5/202; A61B 5/204; A61B 5/205; A61B 5/207; A61B 5/208; A61B 5/00; A61B 8/52–5292; A61B 10/007; A61B 10/0045; A61G 9/00; A61G 9/003; A61G 9/006; A61G 9/102; G06T 2207/30004; G06T 7/0012; G10L 25/66
See application file for complete search history.

(56) References Cited

U.S. PATENT DOCUMENTS 6,582,379 B1 * 6/2003 Stisen .................... A61B 5/208
                                                            600/573
9,743,903 B1 * 8/2017 Hall ....................... A61B 7/008
(Continued)

OTHER PUBLICATIONS

Extended European Search Report dated Aug. 16, 2021 issued in EP 21160344.4.
(Continued)

*Primary Examiner* — Andrew C Flanders
(74) *Attorney, Agent, or Firm* — DLA Piper

(57) ABSTRACT

A system for uroflowmetry is disclosed. The system can include an audio device configured to obtain audio data of urination. The system can include a machine learning module with at least one processor and associated memory, wherein the system is configured to: process the audio data of urination via a machine learning model that is trained based on simulated urine flow data and associated audio data received from a urine flow simulator, and real urine flow data and associated audio data received from a urine flow measuring device, and output the processed audio data of urination to be used in uroflowmetry.

22 Claims, 6 Drawing Sheets

(56) References Cited

U.S. PATENT DOCUMENTS

| | | | | |
|---|---|---|---|---|
| 2006/0020225 A1* | 1/2006 | Gerber | ............... | A61B 5/202 600/561 |
| 2008/0082022 A1* | 4/2008 | Brohan | ............... | A61B 5/208 600/573 |
| 2008/0275366 A1* | 11/2008 | Brohan | ............... | A61B 5/208 600/584 |
| 2011/0125061 A1* | 5/2011 | Shahar | ............... | A61B 5/4381 600/586 |
| 2015/0322663 A1* | 11/2015 | Swendsen | ............... | G10H 1/26 700/94 |
| 2016/0029942 A1* | 2/2016 | Paulsen | ............... | G16H 15/00 702/19 |
| 2016/0220079 A1* | 8/2016 | Abir | ............... | A47K 11/04 |
| 2016/0374619 A1* | 12/2016 | Borkholder | ............... | A61B 5/02055 600/301 |
| 2017/0086728 A1* | 3/2017 | Hidas | ............... | A61B 5/743 |
| 2017/0322197 A1* | 11/2017 | Hall | ............... | G01N 33/493 |
| 2018/0108440 A1* | 4/2018 | Stevens | ............... | G16H 50/20 |
| 2018/0184906 A1* | 7/2018 | Prokopp | ............... | A61B 5/207 |
| 2018/0303466 A1* | 10/2018 | Kashyap | ............... | E03D 11/13 |
| 2019/0212322 A1* | 7/2019 | Tsuruoka | ............... | A61B 5/6887 |
| 2019/0231244 A1* | 8/2019 | Swan | ............... | A61B 5/208 |
| 2019/0285612 A1* | 9/2019 | Sun | ............... | G01N 33/493 |
| 2019/0343444 A1* | 11/2019 | Yabuki | ............... | G01F 23/296 |
| 2019/0365306 A1 | 12/2019 | Laing | | |
| 2019/0365307 A1 | 12/2019 | Laing | | |
| 2019/0365308 A1 | 12/2019 | Laing | | |
| 2020/0015791 A1* | 1/2020 | Mccord | ............... | G01N 33/54386 |
| 2020/0049613 A1* | 2/2020 | Hayashi | ............... | G01N 15/1425 |
| 2020/0054265 A1* | 2/2020 | Song | ............... | A61B 5/208 |
| 2020/0100771 A1* | 4/2020 | Attar | ............... | G01J 3/2803 |
| 2020/0187863 A1* | 6/2020 | Tu | ............... | A61B 5/6891 |

OTHER PUBLICATIONS

Aslim et al. "A Novel Machine-Learning Augmented Audo-Uroflowmetry—Comparison with Standard Uroflowmetry", European Urology Supplements, vol. 18, No. 1, Mar. 2019, p. e1773.

* cited by examiner

SYSTEMS AND METHODS FOR UROFLOWMETRY

FIELD

The present disclosure relates to systems and methods for uroflowmetry.

BACKGROUND

Urological disorders such as obstruction of the lower urinary tract or neurogenic bladder can be detected by studying the patient's urine volumetric flow rate as it varies from the beginning of voiding to the end and the total volume of urine voided. Measurements of flow of the voided amount, for instance, can be useful in diagnosing prostate enlargement, which usually occurs gradually with variable onset and progression of symptoms.

Measurements of volume of the voided amount can be useful to see when during a 24-hour period that urination occurs, how much total urine is produced during a 24-hour period and how much urine is produced, and how frequently, after retiring for the night, another helpful component in the understanding and management of many urologic and non-urologic conditions.

Uroflowmetry, also called a uroflow test, measures the volumetric flow rate of the urine stream during urination as well as the total voided volume in that urination. It is a noninvasive urinary test used to diagnose conditions suggested by symptoms such as urinary frequency, urgency and slow urinary stream. The results of uroflowmetry can help with the assessment of bladder and sphincter function or to test for obstruction to the normal flow of urine.

By measuring the average and maximum rates of urine flow, uroflowmetry can estimate the severity of any blockage or obstruction. It can also help identify other urinary problems, such as a weakened bladder, an overactive bladder, an enlarged prostate, or a urethra obstructed by scar tissue (stricture).

Conditions that are monitored by increased urine output, often after sleep, such as sleep apnea, cardiorenal syndrome, congestive heart failure, diabetes mellitus, and diabetes insipidus are often better managed when precise measurements of the time and the volume amount of each urination are known by the health care team.

The present disclosure provides systems and methods for uroflowmetry that provide technical solutions to the technical shortcomings associated with the known techniques.

SUMMARY

A system for uroflowmetry is disclosed. The system can include an audio device configured to obtain audio data of urination; and a machine learning module with at least one processor and associated memory, wherein the machine learning module is configured to: process the audio data of urination via a machine learning model that is trained based on simulated urine flow data and associated audio data received from a urine flow simulator, and real urine flow data and associated audio data received from a urine flow measuring device, and output the processed audio data of urination to be used in uroflowmetry. In an exemplary embodiment, the audio data of urination can include a sound recording of urine impacting a surface.

In an exemplary embodiment, the urine flow measuring device can include an imaging device configured to capture multiple image frames of urine flow over a time period; one or more processors and associated memory configured to: apply an image segmentation algorithm on each of the image frames to obtain an image segment for each image frame, wherein the image segment includes image pixels associated with the urine flow, and combine consecutive image segments to generate the real urine flow data; and an audio device configured to obtain the associated real audio data of the urine flow.

In an exemplary embodiment, the urine flow can be associated with a human user. The system can include a toilet that receives the urine flow, wherein the imaging device includes two cameras arranged perpendicularly in a plane over the toilet.

In an exemplary embodiment, the urine flow simulator can include a basin that contains water and/or synthetic urine; a pump configured to pump the urine from the basin at one or more volumetric flow rates; a container that receives the urine from the pump to provide the simulated urine flow data; and an audio device configured to obtain the audio data associated with the simulated urine flow data.

In an exemplary embodiment, the system can include a flow meter configured to measure volumetric flow rates of the urine; a tube positioned between the basin and the container, wherein the tube carries the urine from the basin to the container; a display to receive user input to operate the urine flow simulator; and a processor configured to operate the pump to synchronize the volumetric flow rates and associated audio data of the urine. The basin may be temperature controlled and the urine flow simulator may be portable. In an exemplary embodiment, the flow rate may vary between about 0 and 50 ml/s.

A method for uroflowmetry is disclosed. The method can include obtaining audio data of urination from an audio device; processing, via at least one controller, the audio data of urination via a machine learning model that is trained based on simulated urine flow data and associated audio data received from a urine flow simulator, and real urine flow data and associated audio data received from a urine flow measuring device, and outputting the processed audio data of urination to be used in uroflowmetry.

BRIEF DESCRIPTION OF DRAWINGS

Other objects and advantages of the present disclosure will become apparent to those skilled in the art upon reading the following detailed description of exemplary embodiments, in conjunction with the accompanying drawings, in which like reference numerals have been used to designate like elements, and in which.

DESCRIPTION

The present disclosure provides a technique to perform uroflowmetry exams by using a smartphone application or standalone device that can make an audio recording of a person urinating into a toilet. The audio file can be processed with an algorithm that computes a measure of flow rate, among other analytics.

The algorithm can factor in and be robust to background noises, toilet geometries, location and angle of the urine stream's impact, bathroom geometry, location and quality of the microphone, patient sex, urination position (sitting or standing), human physiological variation including patient height, and diameter and shape of the meatus (the urethral opening) among other sources of noise and variation. The results of the processing can be published on a user's smartphone and/or on a physician web portal for remote patient monitoring.

Figure 1:
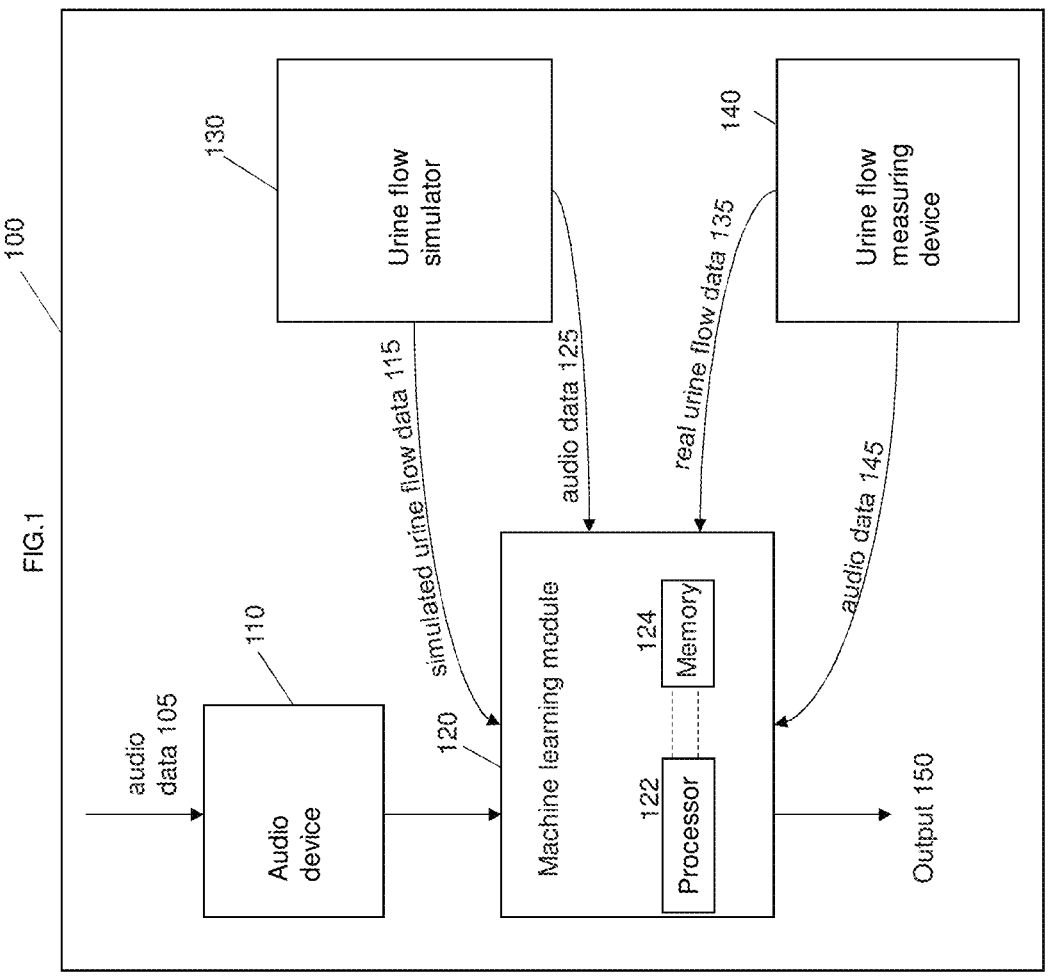
FIG. 1 illustrates a system for uroflowmetry according to an exemplary embodiment of the present disclosure.

FIG. 1 shows an exemplary block diagram for a system 100 for uroflowmetry. The system 100 can include an audio device 110 configured to obtain audio data 105 of urination. The audio 105 data of urination can include a sound recording of urine impacting a surface, such as a surface of toilet bowl water/liquid, a porcelain surface of the toilet bowl, etc.

The audio device 110 can be a microphone that converts urination sound into an electrical signal. In exemplary embodiments, the audio device 110 can be a standalone device or part of another device such as a smartphone. A person of ordinary skill in the art would appreciate that the audio device 110, as used herein, is not limited to a singular device and can include multiple devices.

The audio data 105, as used herein, can be an audio signal that has been recorded in, or converted into, a digital form. The sound wave of the audio signal can be encoded as numerical samples in continuous sequence. In an exemplary embodiment, an analog electrical signal representing a urination sound can be converted with an analog-to-digital converter (ADC) into a digital signal, typically using pulse-code modulation. This digital signal can then be recorded audio data 105 using computers, audio playback machines, and other digital tools.

The system 100 can include a machine learning module 120 with a processor 122 (e.g., a central processing unit (CPU), a graphics processing unit (GPU) or both) and an associated memory 124, such that the machine learning module 120 is configured to process the audio data 105 of urination via a machine learning model (e.g. artificial neural network), and output the processed audio data of urination for uroflowmetry. In an exemplary embodiment, the audio device 110 and the machine learning module 120 can be part of the same electronic device (e.g. a smartphone with a processor/memory and microphone).

As used herein, the term "machine learning" can refer to the various classes of artificial intelligence algorithms and algorithm-driven approaches that are capable of performing machine-driven (e.g., computer-aided) identification of trained structures, with the term "deep learning" referring to a multiple-level operation of such machine learning algorithms using multiple levels of representation and abstraction. However, it will be apparent to a person of ordinary skill in the art that the role of the machine learning algorithms that are applied, used, and configured in the presently described system 100 may be supplemented or substituted by any number of other algorithm-based approaches, including variations of artificial neural networks, learning-capable algorithms, trainable object classifications, and other artificial intelligence processing techniques.

Many variants of convolutional neural networks with varying depth of layers, kernels per layer, number and size of fully connected layers, dropout, pooling etc. can be used. The deep residual network (or a variant) as described in "Deep Residual Learning for Image Recognition", by He et. al. can be used. This is available at https://arxiv.org/pdf/1512.03385.pdf and is incorporated herein by reference. Such a network can be deep as it has identity mappings that pass over the convolutional layers allowing the network to overcome the vanishing gradient problem while training.

A densely connected convolutional network as described in "Densely Connected Convolutional Networks", by Huang et. al. can also be used. This is available at https://arxiv.org/pdf/1608.06993.pdf and is incorporated herein by reference. Similarly, various other feed-forward convolutional neural networks can also be used as the machine learning algorithm.

Human urination profiles contain time correlations (the flow rate at any given time in a human's typical urination is dependent on the previous flow rates). These correlations are ignored by a traditional feed forward network acting on spectrograms from specific time intervals. To leverage this time correlation, the system 100 can introduce recurrence into the machine learning model. A recurrent model operates on sequential data in which previous states of the model can be included into the input at later states. There are many ways to construct recurrent networks from simply including a previous prediction as input to including the previous states of the convolutional layers within the network to higher level structures like LSTMs (long short-term memory recurrent network).

In an exemplary embodiment, the machine learning model can have an option of including extra neurons whose input are data external to the spectrograms. These neurons can be located prior to the final fully connected layers at the final layer of our networks. Non-limiting examples of inputs to these neurons can include the relative amplitude of sound in real space of the time interval corresponding to the spectrogram, the height, age, sex, urination position or other properties of the user, geospatial location or other data.

In an exemplary embodiment, the machine learning model can be trained over the course of many epochs, one pass of the training data. As the training spectrograms are invariant to small translations in the temporal axis, the training data can be randomly translated at each epoch along the temporal axis. An addition of a spectrogram of separately recorded background noise can also be included. This noise can be randomly sampled and has a probability of being added to a given training spectrogram with a randomly sampled amplitude. An echo (e.g. from the toilet, tile floor, ceiling etc.) that may impact the data by appearing as a dampened, time-lagged image of the original signal added to it, can be simulated and randomly added to the training data.

In an exemplary embodiment, the audio data 105 can be converted into a series of spectrograms (at 0.125-0.5 sec intervals), taking the log of the resulting image and normalizing it to zero mean and unit variance as the input to the machine learning model, which can have two neural networks, both similar though not identical in architecture. One may take in the spectrograms and output a class of "pee" or "not pee", determining which times correspond to urination and which do not for each recording. The second algorithm may take in the spectrograms identified as urination and output the flow rate in ml/sec. Combining the two can yield the full uroflowmetry volumetric flow rate profile for the recorded urination.

In an exemplary embodiment, transfer learning techniques can be used such that all or part of the machine learning model can be initialized with parameters from the same or another model or other models trained on a different dataset or for a different task (e.g. using a synthetic dataset as preliminary grounds to train a network on a real dataset). This can serve to increase training efficiency by either reducing the size of a minimum viable training set or amount of time required during training to master the task.

For an optimal result, the machine learning model should be robust to background noises, toilet geometries, location and angle of the urine stream's impact, bathroom geometry, location and quality of the microphone, patient sex, urination position (sitting or standing), human physiological variation including patient height, and diameter and shape of the meatus (the urethral opening) among other sources of noise and variation. To account for all these variations, the present disclosed machine learning model can be trained based on simulated urine flow data 115 and associated audio data 125 received from a urine flow simulator 130, and real urine flow data 135 and associated audio data 145 received from a urine flow measuring device 140. The machine learning model can then output 150 the processed audio data of urination to be used in uroflowmetry. Each of these are described in detail in the present disclosure.

In an exemplary embodiment, the urine flow simulator 130 can be a urinator (e.g. a portable mechanical urinator) that includes a temperature-controlled basin, variable control pump, digital flow meter, variable diameter tubing, adjustable arm, microcontroller, adjustable valves, and a controller computer interface. The pump, which may be regulated by the microcontroller, can continuously step through the full range of physiological flow rates (e.g. from 0 to 50 milliliters per second). The pump may also produce simulated flow profiles imitating realistic urinations. The urine (e.g. synthetic urine) can be drawn from the basin such that it passes through the tubing and flow meter and is emitted into a toilet. The microcontroller may record and synchronize the audio and flow rate data streams to produce the simulated urine flow data 115 and associated audio data 125. The output of the stream may include molded silicone mimicking a variety of meatal diameters and shapes.

In an exemplary embodiment, the urine flow simulator 130 can be a "water clock", which is a device that includes a large tub of temperature-controlled water with an outlet on the bottom through which the synthetic urine would drain slowly over time. The volumetric flow rate coming out of the device can be measured using a beaker and scale (e.g. Laborie device) at various heights of the internal water depth and recorded. This process can be repeated several times. As the flow rates depend on the height of the internal water depth compared to the outlet height, the flow rate over time for the draining of the device can be accurately modeled. This device (water clock) can be placed over various toilets to collect the simulated urine flow data 115 and associated audio data 125 over time.

In an exemplary embodiment, the urine flow simulator 130 can be a highly portable synthetic collection device with a hand pump an and associated controller, a flowmeter at the output of the pump, interchangeable synthetic urethras and meatuses after the flow meter, a microphone associated to the pump as well and a tub of water controlled to body temperature to fill the hand pump in between data collection sessions. Of course, the urine flow simulator 130 can include any combination of the previously described devices, and/or similar devices, and/or multiple devices that generate the simulated urine flow data 115 and associated audio data 125.

The urine flow measuring device 140 can provide real urine flow data 135 and associated real audio data 145 by measuring a rate at which a subject is urinating into a toilet without altering either the state of the subject or the audio signature of the stream impacting the toilet bowl water. The subject, as used herein, can be a human.

Figure 2:
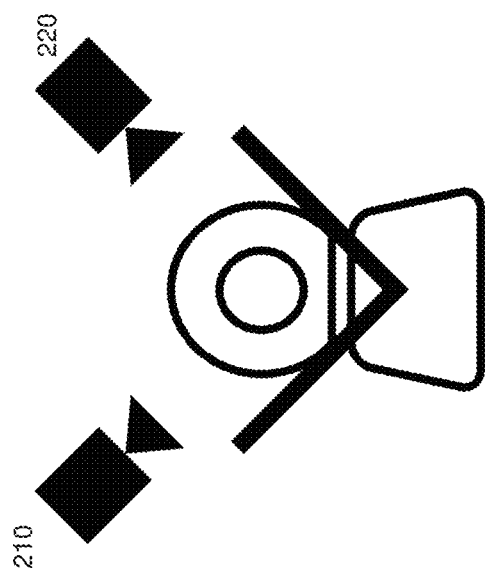
FIG. 2 shows a part of a urine flow measuring device according to an exemplary embodiment of the present disclosure.

FIG. 2 shows a part of an exemplary urine flow measuring device 140 with an imaging device configured to capture multiple image frames of urine flow over a time period. The imaging device can include two high speed cameras 210 and 220 (e.g. Cam 1 and Cam 2) placed perpendicularly in the plane of the surface of a toilet. These cameras capture a subject's urine stream as it enters the toilet. Alternately, a person of ordinary skill in the art would appreciate that a single camera (not shown) can also be used as the imaging device to capture a subject's urine stream as it enters the toilet.

In an exemplary embodiment, an area of the urine droplets captured by the two high speed cameras can be measured to estimate the volume. The image segments per droplets can be tracked to estimate the velocity of the urine stream. Flow rate can be determined as a function of the volume and velocity (e.g. volume*velocity) as described in detail subsequently.

The urine flow measuring device 140 can include a processor configured to apply an image segmentation algorithm on each of the image frames to obtain an image segment for each image frame. Known image segmentation algorithms, for e.g., simple thresholding, canny edge detection, watershed, unet can be used. Exemplary algorithms are described at https://scikit-image.org/docs/dev/user_guide/tutorial_segmentation.html, https://arxiv.org/abs/1505.04597, both incorporated herein by reference.

The image segmentation process can determine which pixels belong to the urine stream and which pixels do not. The obtained image segment can include image pixels associated with the urine flow. From this segmented image, the projected area from the two perpendicularly oriented cameras can be calculated. For example, with an ellipsoidal geometry of the droplets an estimate of the principle semi-axes from its two perpendicular projections can be made. This can then be used to calculate the volume. Similarly, with the connected part of the urine stream as a cylinder with elliptic geometry along its axis of motion (the urine stream has nodes throughout it caused by the surface tension of water that quickly breaks up into droplets after exiting the meatus due to a Plateau-Rayleigh instability).

The total volume along the axis of the velocity of the urine in each frame can be extrapolated yielding a one-dimensional image of volume vs height. Generating this image for each subsequent frame provides an accurate determination of velocity by convolving consecutive frames to assess the volume that has translated in a given amount of time (the cross-correlation will give the displacement, \delta x, in between consecutive frames of known time interval, \delta t, from which we can determine the velocity, v=\delta x/\delta t). The volume can also be measured from tracking the motion of individual droplets of urine within the frames. From these two measurements the real urine flow data 135 can be calculated while simultaneously recording the audio using an audio device to obtain the associated real audio data 145.

Figure 3:
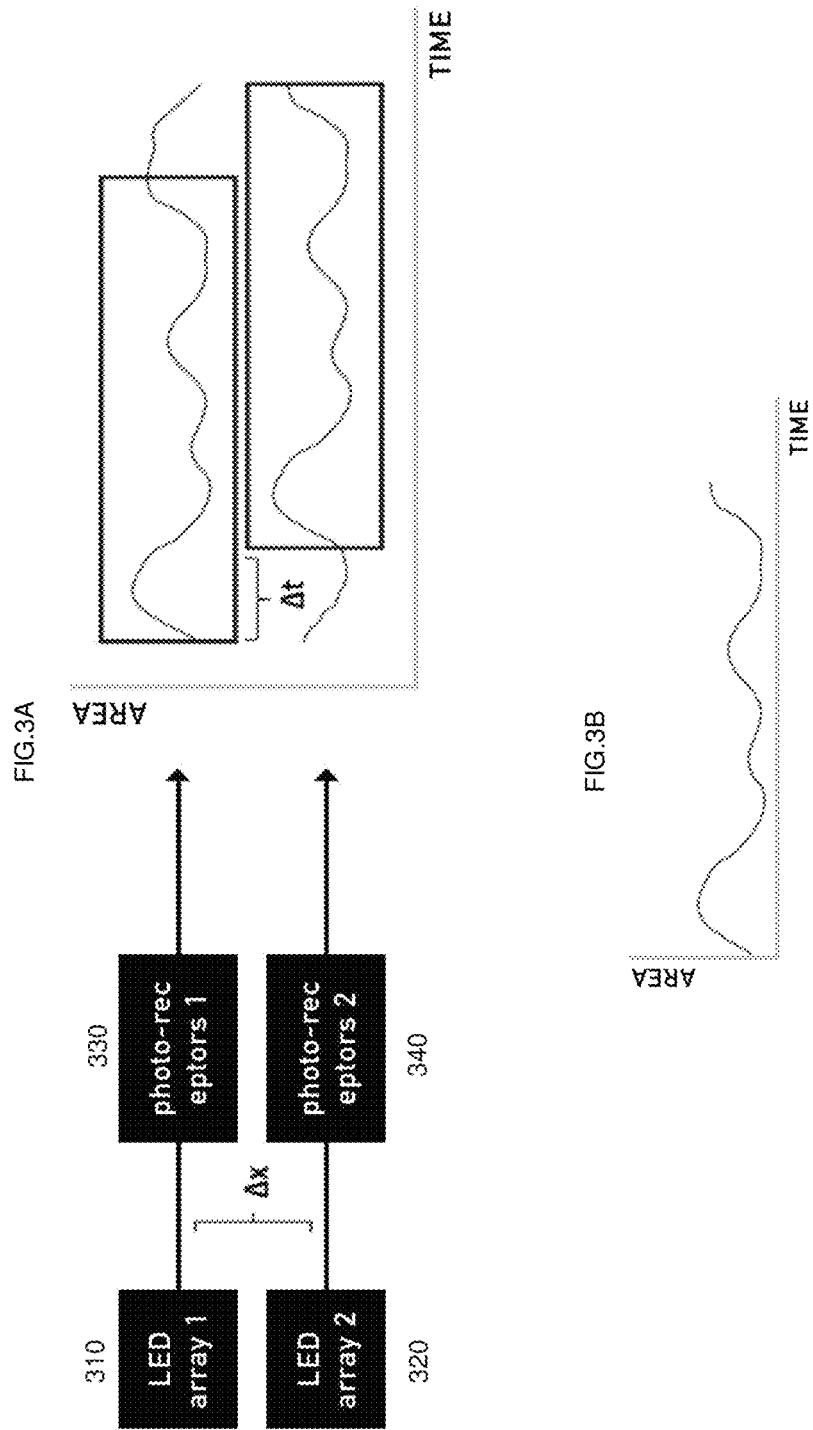
FIG. 3A shows a part of a urine flow measuring device according to an exemplary embodiment of the present disclosure.
FIG. 3B shows a graph for a single LED plane with photoreceptor according to an exemplary embodiment of the present disclosure.

FIG. 3A shows a part of an exemplary LED based urine flow measuring device 140 that includes an array of LEDs 310 and 320 (e.g. LED arrays 1 and 2) producing a plane of light directed at an array of photoreceptors 330 and 340 (e.g. photoreceptors 1 and 2). These photoreceptors (330 and 340) and LEDs (310 and 320) may be positioned so that they all point in one direction, or so that there are two sets perpendicular to one another like the perpendicular cameras or may be positioned uniformly along the interior of a ring for maximum accuracy in area determination.

In an exemplary embodiment, area of urine within the plane of light can be obtained by assuming ellipsoidal symmetry of each droplet/urine stream, and then the area per time at the plane can be calculated. The flow rate, or volume per unit time would be the area under the "area" curve over a given time interval. In an exemplary implementation, when the two planes of light separated by a known distance, \delta x, the area at each plane could be similarly determined and the velocity of the urine could be determined by the known separation, \delta x, and the phase separation, \delta t, in the two area vs time signals. The flow rate would thus be volume/time=area*\delta x/\delta t.

FIG. 3A further shows that with two LED arrays 310 and 320 separated by distance \delta x: the area vs time at each height can be broken into discrete time intervals and the phase separation determines $\Delta t$. Two thin LED sheets directed towards array of receptors 330 and 340 and separated by vertical distance (e.g. $\Delta x$) can measure area of stream at two different heights.

FIG. 3B shows an exemplary graph for a single LED plane with photoreceptor. The volume over time interval is area under the curve for given time interval. "Non-contact measurements of water jet spreading width with a laser instrument" by Funami et al. provides pertinent details of laser based flow rate. This is available at https://doi.org/10.1007/s11630-016-0870-y and is incorporated herein by reference.

Figure 4:
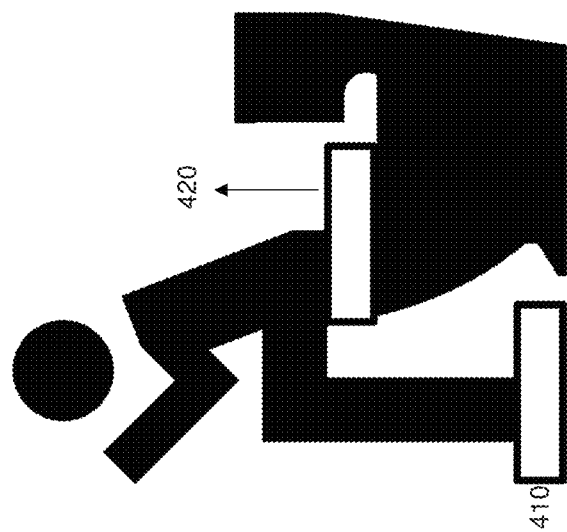
FIG. 4 shows a urine flow measuring device with a digital scale according to an exemplary embodiment of the present disclosure.

FIG. 4 shows exemplary digital scales (e.g. 410 and 420) that may be used with the urine flow measuring device 140. Such a digital scale-based approach may involve a subject sitting on a digital scale while urinating into a toilet, such the digital scale forms part of a scale system including multiple scales. For example, a first scale 410 on the floor can be used to measure the weight of feet. A second scale 420 can be used as a replacement for the seat on the toilet. In some cases, multiple scale sensors can also be placed around the seat to produce a more reliable reading. The digital scales 410 and 420 report a measured weight at each time interval dt. By subtracting the difference of reported weights at neighboring time steps, a flow rate can be computed as (W1−W2)/dt. A person of ordinary skill in the art would appreciate that a similar digital scale-based approach can be used for a subject standing while urinating into a toilet.

Figure 5:
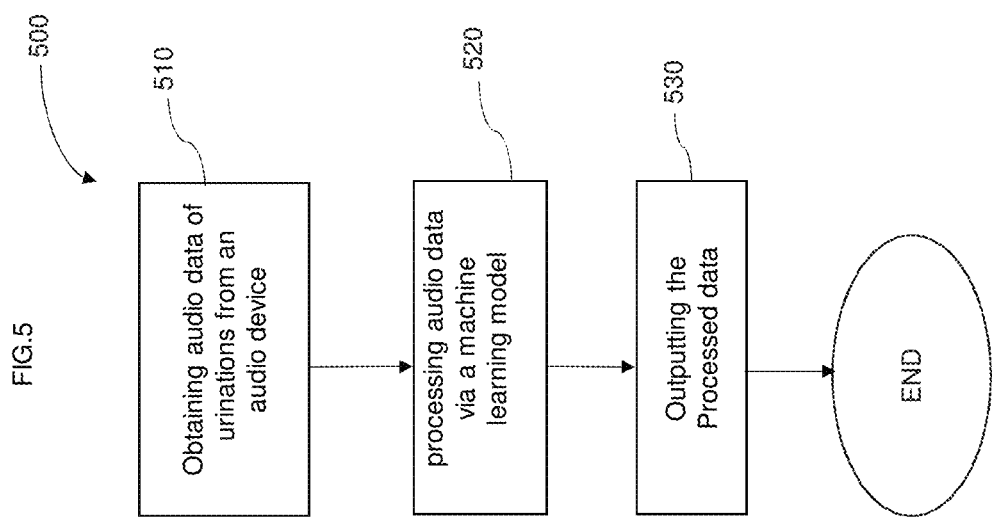
FIG. 5 illustrates flowchart of a method for uroflowmetry according to an embodiment of the present disclosure.

FIG. 5 shows a flowchart of a method 500 for uroflowmetry according to an embodiment of the present disclosure. The method 500 can include a step 510 of obtaining audio data of urination from an audio device. Aspects of the step 510 relate to the previously described audio device 110 of the system 100.

The method 500 can include a step 520 of processing, via at least one controller, the audio data of urination via a machine learning model that is trained based on simulated urine flow data and associated audio data received from a urine flow simulator, and real urine flow data and associated audio data received from a urine flow measuring device. Aspects of the step 520 relate to the previously described machine learning model of the system 100.

The method 500 can include a step 530 of outputting the processed audio data of urination to be used in uroflowmetry. Aspects of the step 530 relate to the previously described output 150 of the system 100. The output results can be published on a user's smartphone and/or on a physician web portal for remote patient monitoring.

In an exemplary embodiment, aspects of the present disclosure (e.g. system 100 and/or method 500) can be implemented on a smartphone application. Such an application can include several views/features described in detail as follows. Data collection view/home screen: the main screen of the application can include a large button that initiates an exam and links to the other views. Medical Information view: here patients may input as much information as they are willing. Some of this data potentially can be used within the machine learning algorithm like height and sex, as previously described with respect to inclusion of extra neurons. Help Information view can include directions and videos teaching a user about the use of the application and performing an exam and links to various reputable sources on the disease that afflicts the user. History view can include data visualizations very similar to that of the physician's patient data view, such as plots of individual urination profiles and calendar plots of various statistics. User input view for inputting events in which the patient was unable to perform an examination and other such information. Messaging view to see messages and notifications from the physician or healthcare professional.

Figure 6:
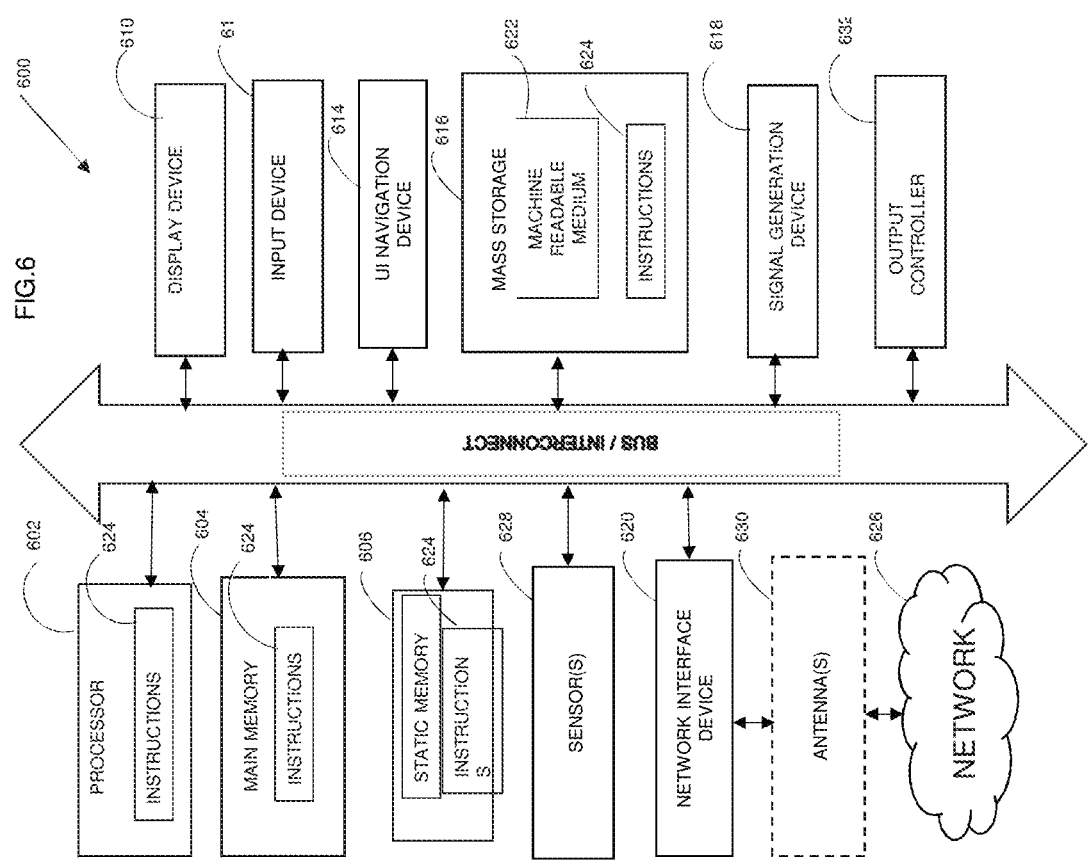
FIG. 6 illustrates an example of a machine configured to perform computing operations according to an embodiment of the present disclosure.

FIG. 6 is a block diagram illustrating an example computing system 600 upon which any one or more of the methodologies (e.g. method 500 or system 100) herein discussed may be run according to an example described herein. Computer system 600 may be embodied as a computing device, providing operations of the components featured in the various figures, including components of the system 100, the audio device 110, the machine learning module 120 with a processor 122 and memory 124, the urine flow simulator 130, the urine flow measuring device 140, or any other processing or computing platform or component described or referred to herein.

In alternative embodiments, the machine can operate as a standalone device or may be connected (e.g., networked) to other machines. In a networked deployment, the machine may operate in the capacity of either a server or a client machine in server-client network environments, or it may act as a peer machine in peer-to-peer (or distributed) network environments.

Example computer system 600 includes a processor 602 (e.g., a central processing unit (CPU), a graphics processing unit (GPU) or both), a main memory 604 and a static memory 606, which communicate with each other via an interconnect 608 (e.g., a link, a bus, etc.). The computer system 600 may further include a video display unit 610, an alphanumeric input device 612 (e.g., a keyboard), and a user interface (UI) navigation device 614 (e.g., a mouse). In one embodiment, the video display unit 610, input device 612 and UI navigation device 614 are a touch screen display. The computer system 600 may additionally include a storage device 616 (e.g., a drive unit), a signal generation device 618 (e.g., a speaker), an output controller 632, and a network interface device 620 (which may include or operably communicate with one or more antennas 630, transceivers, or other wireless communications hardware), and one or more sensors 628.

The storage device 616 includes a machine-readable medium 622 on which is stored one or more sets of data structures and instructions 624 (e.g., software) embodying or utilized by any one or more of the methodologies or functions described herein. The instructions 624 may also reside, completely or at least partially, within the main memory 604, static memory 606, and/or within the processor 602 during execution thereof by the computer system 600, with the main memory 604, static memory 606, and the processor 602 constituting machine-readable media.

While the machine-readable medium 622 is illustrated in an example embodiment to be a single medium, the term "machine-readable medium" may include a single medium or multiple medium (e.g., a centralized or distributed database, and/or associated caches and servers) that store the one or more instructions 624. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 624 may further be transmitted or received over a communications network 626 using a transmission medium via the network interface device 620 utilizing any one of several well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that can store, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the features in the system architecture 900 of the processing system may be client-operated software or be embodied on a server running an operating system with software running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or several components, modules, features, or mechanisms. Such items are tangible entities (e.g., hardware) capable of performing specified operations and may be configured or arranged in a certain manner. In an example, circuits may be arranged (e.g., internally or with respect to external entities such as other circuits) in a specified manner as a module, component, or feature. In an example, the whole or part of one or more computer systems (e.g., a standalone, client or server computer system) or one or more hardware processors may be configured by firmware or software (e.g., instructions, an application portion, or an application) as an item that operates to perform specified operations. In an example, the software may reside on a machine readable medium. In an example, the software, when executed by underlying hardware, causes the hardware to perform the specified operations.

Accordingly, such modules, components, and features are understood to encompass a tangible entity, be that an entity that is physically constructed, specifically configured (e.g., hardwired), or temporarily (e.g., transitorily) configured (e.g., programmed) to operate in a specified manner or to perform part or all operations described herein. Considering examples in which modules, components, and features are temporarily configured, each of the items need not be instantiated at any one moment in time. For example, where the modules, components, and features comprise a general-purpose hardware processor configured using software, the general-purpose hardware processor may be configured as respective different items at different times. Software may accordingly configure a hardware processor, for example, to constitute a particular item at one instance of time and to constitute a different item at a different instance of time.

Additional examples of the presently described method, system, and device embodiments are suggested according to the structures and techniques described herein. Other non-limiting examples may be configured to operate separately or can be combined in any permutation or combination with any one or more of the other examples provided above or throughout the present disclosure.

It will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

The invention claimed is:

1. A system for uroflowmetry, the system comprising:
    a microphone configured to obtain time-varying audio data of urination based on sound pressure; and
    a processor and an associated memory, wherein the processor is configured to:
        process the audio data of urination via a machine learning model that is trained based on simulated urine flow data and associated audio data received from a urine flow simulator, and a human's real-time urine flow data received from a urine flow measuring device and the audio data of urination obtained from the microphone, wherein a state of the real-time urine flow data is unaltered, the machine learning model is a recurrent model that operates on the time-varying audio data such that a state of the model is input to a subsequent state of the model to leverage time correlations in the time-varying audio data, and the time correlations indicate that a current flow rate of urination is dependent on a previous flow rate of urination, and
        output the processed audio data of urination to be used in uroflowmetry.

2. The system of claim 1, wherein the audio data of urination includes a sound recording of urine impacting a surface.

3. The system of claim 1, wherein the urine flow measuring device comprises:
an imaging device configured to capture multiple image frames of urine flow over the time period; and
one or more processors and associated memory configured to:
apply an image segmentation algorithm on each of the image frames to obtain an image segment for each image frame, wherein the image segment includes image pixels associated with the urine flow, and
combine consecutive image segments to generate the real urine flow data.

4. The system of claim 3, wherein the urine flow is associated with a human patient.

5. The system of claim 3, further comprising:
a toilet that receives the urine flow, wherein the imaging device includes two cameras arranged perpendicularly in a plane over the toilet.

6. The system of claim 5, wherein the flow rate varies between about 0 and 50 ml/sec.

7. The system of claim 1, wherein the urine flow simulator comprises:
a basin that contains water and/or synthetic urine;
a pump configured to pump the urine from the basin at one or more volumetric flow rates;
a container that receives the urine from the pump to provide the simulated urine flow data; and
an audio device configured to obtain the audio data associated with the simulated urine flow data.

8. The system of claim 7, further comprising:
a flow meter configured to measure volumetric flow rates of the urine;
a tube positioned between the basin and the container, wherein the tube carries the urine from the basin to the container;
a display to receive user input to operate the urine flow simulator; and
a processor configured to operate the pump to synchronize the volumetric flow rates and associated audio data of the urine.

9. The system of claim 7, wherein the basin is temperature controlled.

10. The system of claim 7, wherein the urine flow simulator is portable.

11. The system of claim 1, wherein the machine learning model is further trained on toilet geometry, location and angle of the urine stream's impact upon the toilet's water surface, location and quality of the microphone, patient sex, urination position, and human physiological variation.

12. A computer-implemented method for uroflowmetry, the method comprising:
obtaining time-varying audio data of urination from a microphone;
processing, via at least one controller, the audio data of urination via a machine learning model that is trained based on simulated urine flow data and associated audio data received from a urine flow simulator, and a human's real-time urine flow data and the audio data of urination obtained from the microphone, wherein a state of the real-time urine flow data is unaltered, the machine learning model is a recurrent model that operates on the time-varying audio data such that a state of the model is input to a subsequent state of the model to leverage time correlations in the time-varying audio data, and the time correlations indicate that a current flow rate of urination is dependent on a previous flow rate of urination, and
outputting the processed audio data of urination to be used in uroflowmetry.

13. The method of claim 12, wherein the audio data of urination includes a sound recording of urine impacting a surface.

14. The method of claim 12, wherein the urine flow measuring device comprises:
an imaging device configured to capture multiple image frames of urine flow over the time period;
one or more processors and associated memory configured to:
apply an image segmentation algorithm on each of the image frames to obtain an image segment for each image frame, wherein the image segment includes image pixels associated with the urine flow, and
combine consecutive image segments to generate the real urine flow data.

15. The method of claim 14, wherein the urine flow is associated with a human patient.

16. The method of claim 14, further comprising:
receiving the urine flow at a toilet, wherein the imaging device includes two cameras arranged perpendicularly in a plane over the toilet.

17. The method of claim 12, wherein the urine flow simulator comprises:
a basin that contains water and/or synthetic urine;
a pump configured to pump the urine from the basin at one or more volumetric flow rates;
a container that receives the urine from the pump to provide the simulated urine flow data; and
an audio device configured to obtain the audio data associated with the simulated urine flow data.

18. The method of claim 17, wherein the urine flow simulator comprises:
a flow meter configured to measure volumetric flow rates of the urine;
a tube positioned between the basin and the container, wherein the tube carries the urine from the basin to the container;
a display to receive user input to operate the urine flow simulator, wherein the one or more processors are configured to operate the pump to synchronize the volumetric flow rates and associated audio data of the urine.

19. The method of claim 17, wherein the basin is temperature controlled.

20. The method of claim 17, wherein the urine flow simulator is portable.

21. The method of claim 17, wherein the flow rate varies between about 0 and 50 ml/sec.

22. The method of claim 12, wherein the machine learning model is further trained on toilet geometry, location and angle of the urine stream's impact upon the toilet's water surface, location and quality of the microphone, patient sex, urination position, and human physiological variation.

* * * * *